United States Patent [19]

Jordan et al.

[11] Patent Number: 5,495,035
[45] Date of Patent: Feb. 27, 1996

[54] SYNTHESIS OF ANSA-METALLOCENE CATALYSTS

[75] Inventors: Richard F. Jordan, Iowa City, Iowa; Stephan Rodewald, Teddington, United Kingdom; Gary M. Diamond, Iowa City, Iowa

[73] Assignee: University of Iowa Research Foundation, Iowa City, Iowa

[21] Appl. No.: 252,591

[22] Filed: Jun. 1, 1994

[51] Int. Cl.$^6$ .............. C07F 17/00; C07F 5/00; C07F 9/00
[52] U.S. Cl. .............. 556/1; 556/43; 556/53; 534/15
[58] Field of Search ............... 556/53, 43, 1; 534/11, 15

[56] References Cited

U.S. PATENT DOCUMENTS

| | | | |
|---|---|---|---|
| 4,042,610 | 8/1977 | Manzer | 260/429.3 |
| 4,855,468 | 8/1989 | Riediker et al. | 556/53 |
| 4,956,323 | 9/1990 | Hefner | 502/113 |
| 5,145,819 | 9/1992 | Winter et al. | 502/117 |
| 5,194,532 | 3/1993 | Hefner et al. | 526/126 |
| 5,208,304 | 5/1993 | Waymouth | 526/164 |
| 5,264,405 | 11/1993 | Canich | 502/103 |
| 5,268,495 | 12/1993 | Riepl et al. | 556/11 |
| 5,279,999 | 1/1994 | DeBoer et al. | 502/117 |

FOREIGN PATENT DOCUMENTS

0530908A1 3/1993 European Pat. Off. .

OTHER PUBLICATIONS

Walter Spaleck et al., *Organometallics* 1994, 13 954–963.
Udo Stehling et al., *Organometallics* 1994, 13, 964–970.
Walter Kaminsky et al., *Makromol Chem.* 193, 1643–1651 (1992).
John A. Ewen et al., *Makromol Chem., Macromol Symp.* 48/49, 253–295 (1991).
Ronald L. Halterman, *Chem. Rev.* 1992, 92, 965–994.
William W. Ellis et al., *Organometallics* 1993, 12, 4391–4401.
Robert B. Grossman et al., *Organometallics* 1991, 10, 1501–1505.
Scott Collins et al., *Org. Chem.* 1989, 54, 4154–4158.
Scott Collins et al., *Journal of Organometallic Chemistry*, 342 (1988) 21–29.
Ferdinand R. W. P. Wild et al., *Journal of Organometallic Chemistry* 288 (1985) 63–67.
Scott Collins et al., *Organometallics* 1991, 10, 2349–2356.
Mark S. Erickson et al., *Journal of Organometallic Chemistry* 415 (1991) 75–85.
Helga Wiesenfeldt et al., *Journal of Organometallic Chemistry*, 369 (1989) 359–370.
D. C. Bradley et al., *Proc. Chem. Soc.*, 1959, 225–226.
D. C. Bradley et al., *J. Chem. Soc.*, 1960, 3857–3861.
G. Chandra et al., *J. Chem. Soc.(A)*, 1968, 1940–1945.
Andrew K. Hughes et al., *Organometallics* 1993, 12, 1936–1945.
K. Issleib et al., *Z. Anorg. Allg. Chem.*, vol. 369, (1969) pp. 83–88.
Dormond, et al., Journal of Organometallic Chemistry, 210 (1981) 83–90.

*Primary Examiner*—Porfirio Nazario-Gonzales
*Attorney, Agent, or Firm*—Zarley, McKee, Thomte, Voorhees, & Sease

[57] ABSTRACT

A process of preparing in high yield ansa-metallocene complexes and rac-ansa-metallocene complexes by reacting an ansa-bis-cyclopentadiene compound with a metal amide complex.

20 Claims, No Drawings

SYNTHESIS OF ANSA-METALLOCENE CATALYSTS

GRANT REFERENCE

The invention here set forth was partially funded by the National Science Foundation Grant #CHE90-22700 Amend 02 and the government may have certain rights in the invention. The invention was also partially funded by the Department of Energy Grant No. DE-FG 02-88ER13935.

BACKGROUND OF THE INVENTION

This invention relates to the field, now well established, of use of ansa-metallocenes as catalysts. They are particularly useful as catalysts for the polymerization of ethylene and alpha olefins such as propylene.

Conventional heterogeneous catalysts such as Ziegler-Natta systems have a variety of active sites, only some of which are stereo-specific. Obtaining a polymer with specific properties can involve a considerable amount of trial and error in order to find the best combination of catalyst, co-catalyst and stereo-regulator. In contrast, however, the active polymerization site in a metallocene catalyst is well defined, and can be modified in a straightforward manner via modification by the cyclopentadienyl ligands, enabling the structure of the polymer to be controlled with far greater precision.

A simple metallocene catalyst for polymerizing ethylene is $(C_5H_5)_2ZrCl_2$ which consists of a zirconium atom bound to two chlorine atoms and two cyclopentadienyl rings, and which is activated by co-catalysts such as methylaluminoxane (MAO). During the 1980's, ansa or bridged metallocenes, in which the cyclopentadienyl rings are linked by a chemical bridge, were found to be particularly useful for the polymerization of olefins. In particular, ansa-metallocene complexes, when used in combination with a co-catalyst such as methylaluminoxane (MAO), polymerize propylene to highly isotactic polypropylene, highly syndiotactic polypropylene, or atactic polypropylene, depending on the structure of the ansa-metallocene used.

As is well known, isotactic polymers have each pendant group attached to the backbone in the same orientation, whereas in syndiotactic polymers, these groups alternate in their orientations and atactic polymers have a random arrangement of the groups along the backbone. Since the stereochemistry of the polymer has a great effect on its properties, it is desirable to control this feature. Chiral, $C_2$-symmetric ansa-metallocenes produce isotactic polypropylene.

While the greatest area of potential use for ansa-metallocene catalysts currently is for polymerization of olefins, such as ethylene and propylene, they also have significant uses as catalysts or catalyst precursors for other reactions where stereo-selectivity is important.

The utility of ansa-metallocene complexes as catalysts for olefin polymerization and other reactions has created a high demand for a practical synthesis of ansa-metallocene compounds.

In spite of this demand, current procedures for the synthesis of Group 4 (Ti,Zr,Hf) ansa-metallocenes require the use of ansa-bis-cyclopentadienyl dianion reagents and are hampered by low yields and tedious isomer separation and purification steps. Some of these problems have been discussed in Ellis, W. W.; Hollis, T. K.; Odenkirk, W., Whelan, J.; Ostrander, R.; Rheingold, A. L.; Bosnich, B. *Organometallics* 1993, 12, 4391. In particular, the synthesis of chiral $C_2$ symmetric ansa-metallocenes typically produces mixtures of desired rac (racemic) and undesired meso isomers. A typical synthesis of an ansa-metallocene complex is shown in equation 1 below:

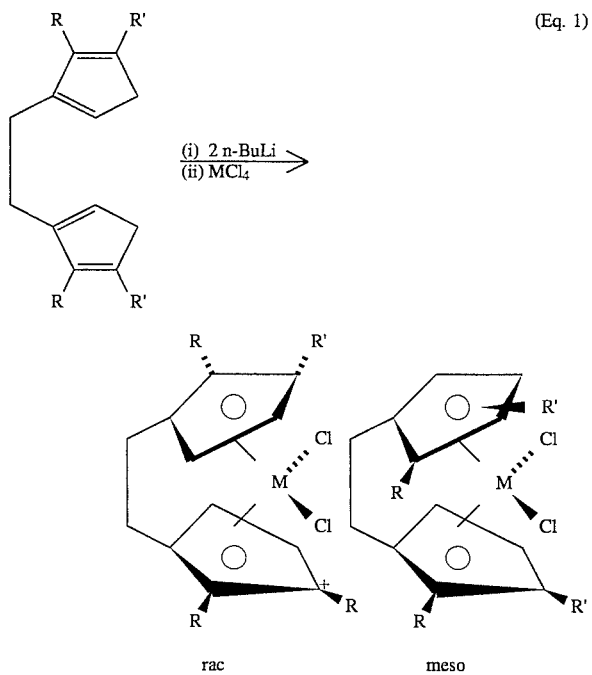

(Eq. 1)

rac    meso

This equation is typical of the process as shown in the art. See for example Spaleck, W.; Kuber, F., Winter, A.; Rohrman, J.; Bachmann, B.; Antberg, M.; Dolle, V.; Paulus, E. F. *Organometallics* 1994, 13, 954. Stehling, U.; Diebold, J.; Kirsten, R.; Roll, W.; Brintzinger, H. H.; Jungling, S.; Mulhaupt, R.; Langhauser, F. *Organometallics* 1994, 13, 964. Halterman, R. L. Chem. Rev. 1992, 92, 965. See also, for example, U.S. Pat. No. 5,145,819, U.S. Pat. No. 5,268, 495, and EPA 0-530-908-A1.

By way of further example, an important chiral Group 4 ansa-metallocene is rac-(EBI)ZrCl2 (EBI=ethylene-1,2-bis(1-indenyl) which is currently prepared from $ZrCl_4$ and the dianion of the EBI ligand (Halterman, R. L. *Chem. Rev.* 1992, 92, 965). Brintzinger (Wild, F. R. W. P.; Wasiucionek, M.; Huttner, G., Brintzinger, H. H. J. *Organomet. Chem.* 1985, 288, 63) and Collins (Collins, S.; Kuntz, B. A.; Hong, Y. J. *Org. Chem.* 1989, 54, 4154; Collins, S.; Kuntz, B. A.; Taylor, N. J.; Ward, D. G. J. *Organomet. Chem.* 1988, 342, 21) used $(EBI)Li_2$ and reported low, variable yields (20-50%) of rac-$(EBI)ZrCl_2$. Buchwald employed $(EBI)K_2$ and obtained $(EBI)ZrCl_2$ in a rac/meso ratio of 2/1 in 70% yield. Grossman, R. B.; Doyle, R. A.; Buchwald, S. L. *Organometallics* 1991, 10, 1501. In general, current synthetic procedures produce the desired rac ansa-metallocenes in 10%–30% yield after tedious separation and purification steps, and even then separation of the rac from the meso products is not always possible.

Lappert et al. (Chandra, G.; Lappert, M. F. *J. Chem Soc.* (A) 1968, 1940) reported that certain Group 4 metallocene complexes are formed by the reaction of Group 4 metal amide complexes with cyclopentadiene compounds. However, this reaction yields only mono-cyclopentadienyl products when the metal is titanium, or when the cyclopentadiene compound is indene. This was ascribed to steric hindrance which disfavors addition of the second cyclopentadienyl ligand when the metal is small (titanium) or the cyclopentadienyl ligand is bulky (indenyl). Hefner, et al., also (U.S. Pat. No. 5,194,532) discusses the preparation of (indenyl)Ti(NMe$_2$)$_3$ by reaction of indene and Ti(NMe$_2$)$_4$. Ansa-metallocene complexes are not discussed in the Lappert or Hefner references.

There is, therefore, a need for a process which would produce ansa-metallocene complexes in high yield. Additionally, there is a need for a process which would produce rac ansa-metallocenes in high yield without contamination by the meso isomer, since the rac isomer is most useful in stereoselective catalysis. The present invention has as its primary objectives the fulfillment of these needs.

It is another objective of the present invention to prepare rac ansa-metallocenes by means of a single step process, in most instances in yields of 70% or higher, without the use of ansa-bis-cyclopentadienyl dianion reagents.

SUMMARY OF THE INVENTION

The process of preparing rac ansa-metallocene complexes in high yield by reacting an ansa-bis-cyclopentadiene, indene, fluorene, or substituted derivative thereof with a metal amide complex wherein the metal is a Group 4 metal, preferably zirconium, and R and R' (eq. 2) are preferably hydrogen or $C_1$ to $C_{20}$ hydrocarbyl radicals, and more preferably $C_1$ to $C_4$ alkyl and most preferably methyl.

DETAILED DESCRIPTION OF THE INVENTION

In the present invention, ansa-metallocene complexes of general formula

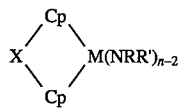

are prepared by reaction of metal amide complexes with ansa-bis-cyclopentadiene compounds as illustrated in eq. 2.

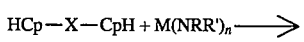  (Eq. 2)

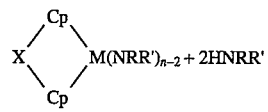

R and R' represent hydrogen or hydrocarbyl radicals having from 1 to 20 carbon atoms, preferably from 1 to 4 carbon atoms. R and R' may also be silyl radicals SiR$_3$. R and R' may be linked.

Cp independently in each occurrence is a cyclopentadienyl, indenyl, fluorenyl or related group that can π-bond to the metal, or a hydrocarbyl, alkyl, aryl, silyl, halo, halohydrocarbyl, hydrocarbylmetalloid, or halohydrocarbylmetalloid substituted derivative thereof. Cp may contain up to 75 nonhydrogen atoms.

X may be any bridging or ansa group that is used to link the Cp groups, including, for example, silylene (—SIR$_2$≲), benzo (C$_6$H$_4$) or substituted benzo, methylene (—CH$_2$) or substituted methylene, ethylene (—CH$_2$CH$_2$—), or substituted ethylene bridges.

M represents the metal used and is usually a Group 4 metal selected from the group consisting of titanium, zirconium and hafnium, but may also be a Group 3 (Sc,Y,La), Group 5 (V,Nb,Ta), Lanthanide or Actinide metal. Preferably it is a Group 4 metal, and most preferably it is zirconium.

n is a whole number and is from 3 to 5. When M is a Group 4 metal or an Actinide "n" is 4, when M is a Group 3 or Lanthanide metal "n" is 3, and when M is a Group 5 metal "n" is 5.

In particular, the rac isomers of chiral C$_2$-symmetric ansa-metallocenes are prepared in high yield. An example is the reaction of Zr(NMe$_2$)$_4$ with (EBI)H$_2$, shown below (eq. 3). This reaction provides an efficient, high yield synthesis of pure rac-(EBI)Zr(NMe$_2$)$_2$, which can easily be converted to rac-(EBI)ZrCl$_2$ and related derivatives.

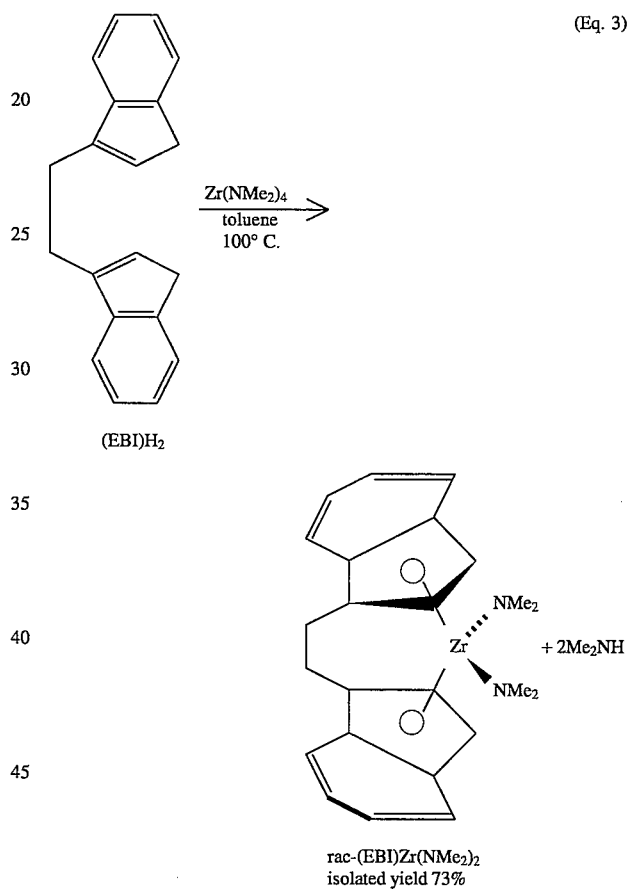

The process of making each starting material for this reaction is known. In particular, the synthesis of ansa-bis-cyclopentadienes such as (EBI)H$_2$ is described in Halterman, R. L. Chem. Rev. 1992, 92, 965, and references therein.

The metal amide complexes M(NR'R')$_4$ can be prepared by reacting the corresponding metal tetrahalide complex such as zirconium tetrachloride with an appropriate lithium amide, see D. C. Bradley and I. M. Thomas, Proc. Chem. Soc., 1959, 225; J. Chem. Soc. 1960, 3857. As earlier indicated, it is preferred that R and R' be hydrogen or $C_1$ to $C_{20}$ hydrocarbyl radicals and preferably $C_1$ to $C_4$. Methyl is the most preferred and is illustrated in eq. 3.

The reaction between the ansa-bis-cyclopentadiene and the metal amide can take place at any temperature from ambient, i.e., about 25° C. up to 250° C., preferably within the range of 80° C. to 125° C. At 100° C. the reaction is typically complete in less than 24 hours, and perhaps as few as 3 to 5 hours. The reaction is unaffected by room light and appears to be reversible.

The dimethylamine produced as a by-product in eq. 3 is gaseous. It is preferred that this not be completely swept away by gas flushing during the reaction as it is believed that it may catalyze the conversion of initially formed meso product to the desired rac product, therefore, ultimately yielding a higher ratio of rac/meso. This is believed the case because it has been observed that when the reaction flask is flushed with inert gas during the reaction, the yield of desired rac product decreases significantly.

While the use of metal amide complexes as starting materials is discussed above, if the NRR' groups are replaced with PRR' or SR groups, it is expected that equivalent results will be achieved. Likewise, amide complexes of the Group 3 metals, (Sc,Y,La), Group 5 metals (V,Nb,Ta) and the Actinides and Lanthanides may also be used, and it is expected that equivalent results will be achieved.

It is also expected that use of chiral, enantiomerically enriched metal amide complexes in equation 2 will allow the synthesis of enantiomerically enriched ansa-metallocenes.

The reaction desirably is conducted in the presence of a nonaqueous, nonalcoholic, solvent that at least partially dissolves one of the reactants. Typical of such solvents are hydrocarbons such as benzene, toluene, and hexane, simple ethers, chlorinated hydrocarbons, acetonitrile, tetrahydrofuran, etc.

It is believed that the metallocene amido complexes which are produced in eq. 2 may, when activated by a suitable cocatalyst, be used as catalysts in many applications. Alternatively, the metallocene amido complexes which are produced in eq. 2 may be converted to the more commonly used metallocene chloride complexes by a simple protonation reaction as described in Hughes, A. K.; Meetsma, A.; Teuben, J. H., *Organometallics* 1993, 12, 1936.

The following examples are offered to further illustrate but not limit the process of the present invention.

EXAMPLE

The ansa-metallocene rac-(EBI)Zr(NMe$_2$)$_2$ has been prepared in high yield from Zr(NMe$_2$)$_4$ and (EBI)H$_2$ (eq. 3). In a typical reaction, under N$_2$ atmosphere, Zr(NMe$_2$)$_4$ (0.50 g, 1.9 mmol) and (EBI)H$_2$ (0.48 g, 1.9 mmol) were placed in a Schlenk vessel containing a Teflon stir bar. Toluene (50 ml) was added. The reaction mixture was stirred and heated to 100° C. for 17 hours. During this period, the HNMe$_2$ co-product was allowed to escape freely (via an oil bubbler) from the reaction vessel. Removal of solvent under reduced pressure afforded an orange solid which was shown by $^1$H NMR to be (EBI)Zr(NMe$_2$)$_2$ in a rac/meso ration of 10/1, in 90% yield. Recrystallization from hexane afforded pure rac-(EBI)Zr(NMe$_2$)$_2$ in 73% isolated yield (0.59 g). The rac-(EBI)Zr(NMe$_2$)$_2$ was characterized by $^1$H and $^{13}$C NMR, elemental analysis, and an X-ray crystal structure determination.

It was also shown that rac-(EBI)Zr(NMe$_2$)$_2$ reacts with two equivalents of Me$_2$NH.HCl to give rac-(EBI)ZrCl$_2$ in high isolated yield (eq.4). In a typical reaction, under N$_2$ atmosphere, a solution of Me$_2$NH.HCl (0.093 g, 1.14 mmol) in CH$_2$Cl$_2$ (20 ml) was added dropwise to a stirred solution of rac-(EBI)Zr(NMe$_2$)$_2$ (0.25 g, 0.57 mmol) at −78° C. The resulting clear, yellow solution was stirred at room temperature for 30 mins. The solvent was removed under reduced pressure and the resulting solid was washed with hexane (15 ml) and extracted with toluene (70 ml). Removal of the solvent from the toluene extract under reduced pressure gave pure rac-(EBI)ZrCl$_2$ in 92% isolated yield (0.22 g). (Eq. 4)

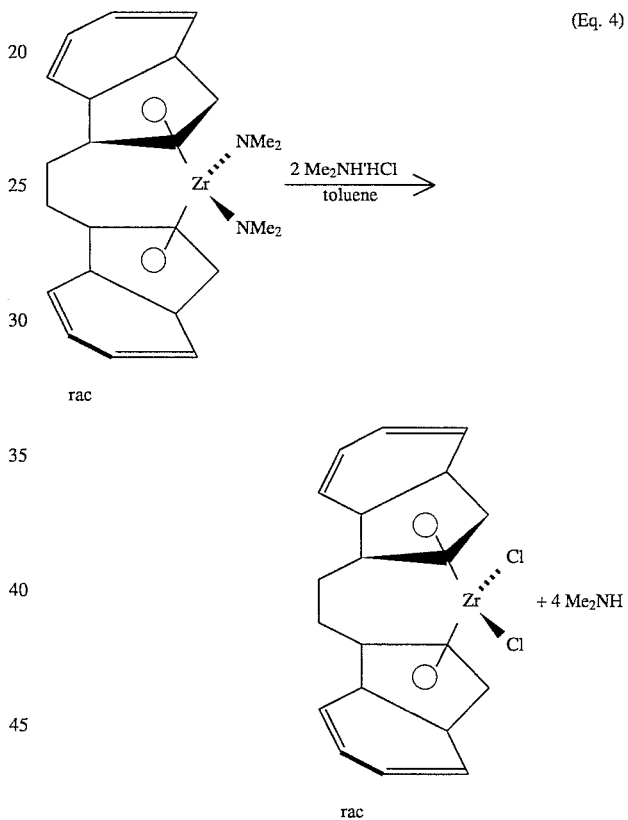

The following additional examples were run using the basic synthesis shown in Example 1 and are presented here for succinctness in table form.

TABLE

Synthesis of rac-(EBI)Zr(NMe$_2$)$_2$ in high yield.

| Example No. | solvent | temp (°C.) | reaction time (hours) | system used | (EBI)Zr(NMe$_2$)$_2$ as % of crude product | rac/meso ratio of crude product | % isolated rac-(EBI)Zr(NMe$_2$)$_2$ (crystallized from) |
|---|---|---|---|---|---|---|---|
| 2 | toluene | 100 | 48 | N$_2$ purge[a] | 90 | 1/1 | 25 (toluene) |
| 3 | toluene | 100 | 26 | partial N$_2$ purge[b] | 80 | 4/1 | — |
| 4 | toluene | 100 | 17 | N$_2$ | 90 | 1/1 | — |

TABLE-continued

Synthesis of rac-$(EBI)Zr(NMe_2)_2$ in high yield.

| Example No. | solvent | temp (°C.) | reaction time (hours) | system used | $(EBI)Zr(NMe_2)_2$ as % of crude product | rac/meso ratio of crude product | % isolated rac-$(EBI)Zr(NMe_2)_2$ (crystallized from) |
|---|---|---|---|---|---|---|---|
| 5 | chlorobenzene | 125 | 17 | purge(a) open(c) | 90 | 9/1 | 70 (hexane) |
| 6 | toluene | 100 | 117 | open(c) | <60 | 60/1 | — |
| 7 | toluene | 100 | 12 | pressure release(d) | 85 | 10/1 | 75 (toluene) |
| 8 | toluene | 100 | 18 | closed(e) | 50 | 1/1 | — |
| 9 | toluene | 100 | 17 | open(c) | 90 | 13/1 | 68 (toluene) |
| 10 | toluene | 100 | 18 | open dark(f) | 90 | 13/1 | — |
| 11 | THF | 67 | 20 | open(c) | 50 | 2/1 | — |

(a)$N_2$ bubbled through reaction solution to drive off $HNMe_2$ as it is formed
(b)$N_2$ bubbled through reaction solution only for part of reaction time
(c)$HNMe_2$ allowed to escape freely (via an oil bubbler) from reaction vessel
(d)$HNMe_2$ allowed to escape from reaction vessel via a mercury bubbler
(e)closed system, $HNMe_2$ is retained in reaction vessel
(f)as for (c) except reaction vessel wrapped in aluminum foil to exclude light It can therefore be seen that the invention accomplishes all of its stated objectives in that ansa-metallocenes were prepared in pure rac form in high yields without the use of ansa-bis-cyclopentadienyl dianion reagents. The yields are substantially higher than the traditional prior art yields of 10% to 30%.

What is claimed is:

1. A process of synthesizing in high yield ansa-metallocene complexes of the formula:

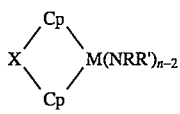

wherein Cp independently and in each occurrence is cyclopentadienyl, indenyl, or fluorenyl, or a related group that can π-bond to the metal, or a hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl or related group, X is a bridging group which links the Cp groups, M is a metal selected from the group consisting of Group 3, 4, and 5 metals, R and R' are the same or different and are each hydrogen or hydrocarbyl radicals of from $C_1$ to $C_{20}$, or silyl radicals, and n is from 3 to 5, said process comprising: reacting an ansa-bis Cp compound of the formula HCp—X—CpH where Cp and X are as above defined with a metal amide complex to provide a high yield of ansa-metallocene complex.

2. The process of claim 1 wherein the Group 4 metal is selected from the group consisting of zirconium, titanium and hafnium.

3. The process of claim 2 wherein the metal is zirconium.

4. The process of claim 1 wherein R and R' are independently $C_1$ to $C_4$ alkyl.

5. The process of claim 4 wherein R and R' are methyl and the gaseous byproduct dimethylamine is not swept away from the reaction as it is produced.

6. The process of claim 1 wherein said process is conducted at a temperature ranging from 25° C. to 250° C.

7. The process of claim 1 wherein said process is conducted at a temperature ranging from 80° C. to 125° C.

8. The process of claim 1 wherein the reaction is conducted in the presence of a nonaqueous, nonalcoholic organic solvent.

9. The process of claim 8 wherein the solvent is selected from the group consisting of hydrocarbons, toluene, ethers, chlorinated hydrocarbons and tetrahydrofuran.

10. The process of claim 1 where X is ethylene and Cp is indenyl.

11. A process of synthesizing in high yield ansa-metallocene complexes of the formula:

wherein Cp independently and in each occurrence is cyclopentadienyl, indenyl, or fluorenyl, or a related group that can π-bond to the metal, or a hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl or related group, X is a bridging group which links the Cp groups, M is a metal selected from the group consisting of Group 3, 4, and 5 metals, R and R' are the same or different and are each hydrogen or hydrocarbyl radicals of from $C_1$ to $C_{20}$, or silyl radicals, and n is from 3 to 5, said process comprising: reacting an ansa-bis Cp compound of the formula HCp—X—CpH where Cp and X are as above defined with a metal amide complex to provide a high yield of ansa-metallocene complex; and thereafter, isolating the ansa-metallocene complex from the reaction mixture.

12. The process of claim 11 wherein the metal is a Group 4 metal and n is 4.

13. The process of claim 12 wherein the metal is zirconium and n is 4.

14. The process of claim 11 wherein R and R' are both methyl.

15. The process of claim 14 wherein X is an ethylene moiety and Cp is indenyl.

16. The process of claim 11 wherein R and R' are methyl and the gaseous byproduct dimethylamine is not swept away from the reaction as it is produced.

17. A process of synthesizing in high yield rac ansa-metallocene complexes of the formula:

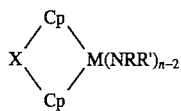

wherein Cp independently and in each occurrence is a hydrocarbyl, alkyl, aryl, silyl, halo, halohydrocarbyl, hydrocarbylmetalloid, or halohydrocarbylmetalloid substituted cyclopentadienyl, an indenyl, a fluorenyl, or a related group that can π-bond to the metal, or a hydrocarbyl, alkyl, aryl, silyl, halo, halohydrocarbyl, hydrocarbylmetalloid, or halohydrocarbylmetalloid substituted derivative of said indenyl, fluorenyl, or related group, X is a bridging group which links the Cp groups, M is a metal selected from the group consisting of Group 3, 4, and 5 metals, R and R' are the same or different or linked and are each hydrogen or hydrocarbyl radicals of from $C_1$ to $C_{20}$, or silyl radicals, and n is from 3 to 5, said process comprising: reacting a hydrocarbyl, alkyl, aryl, silyl, halo, halohydrocarbyl, hydrocarbylmetalloid, or halohydrocarbylmetalloid substituted ansa-bis-cyclopentadiene, or an ansa-bis-indene, or an ansa-bis-fluorene or a related group that can π-bond to the metal, or a hydrocarbyl, alkyl, aryl, silyl, halo, halohydrocarbyl, hydrocarbylmetalloid, or halohydrocarbylmetalloid substituted derivative of said ansa-bis-indene, ansa-bis-fluorene or related group, with a metal amide complex to provide a high yield of rac ansa-metallocene complex.

18. The process of claim 17 which includes as an additional step isolating the rac ansa-metallocene complex.

19. The process of claim 18 wherein X is ethylene and Cp is indenyl.

20. The process of claim 1 which includes a step of converting the ansa-metallocene amido complex to an ansa-metallocene chloride complex.

* * * * *